United States Patent [19]

Jonckers

[11] Patent Number: 4,801,747
[45] Date of Patent: Jan. 31, 1989

[54] PROCESS FOR PREPARING UREA
[75] Inventor: Kees Jonckers, Born, Netherlands
[73] Assignee: Stamicarbon B.V., Geleen, Netherlands
[21] Appl. No.: 898,610
[22] Filed: Oct. 6, 1986

Related U.S. Application Data

[63] Continuation of Ser. No. 670,731, Nov. 13, 1984, abandoned.

[30] Foreign Application Priority Data

Nov. 13, 1983 [NL] Netherlands .......................... 8303888

[51] Int. Cl.$^4$ .................... C07C 126/08; C07C 126/02
[52] U.S. Cl. ......................................... 564/72; 564/71; 564/73
[58] Field of Search ............................. 564/71, 73, 72

[56] References Cited

U.S. PATENT DOCUMENTS

| | | | |
|---|---|---|---|
| 3,137,725 | 6/1964 | Cook et al. | 564/71 |
| 3,366,682 | 1/1968 | Heunks | 564/71 |
| 4,207,256 | 6/1980 | Inoue et al. | 564/71 |
| 4,354,040 | 10/1982 | Inoue et al. | 564/71 X |

Primary Examiner—Glennon H. Hollrah
Assistant Examiner—Carolyn S. Greason
Attorney, Agent, or Firm—Cushman, Darby & Cushman

[57] ABSTRACT

An improved process for the preparation of urea from carbon dioxide and excess ammonia at an elevated temperature and pressure to form a urea synthesis solution containing uncoverted ammonium carbamate and free ammonia. A portion of the ammonium carbamate contained in the urea synthesis solution is decomposed in a first decomposition zone by the supply of heat, and the first gas mixture thus obtained is separated and at least partially condensed in a first condensation zone. The residual area solution is heated in a second decomposition zone maintained at a pressure of between about 4 and 40 bar thereby decomposing a further portion of ammonium carbamate and the second gas mixture thus obtained is separated from the second residual urea containing stream. This second residual area stream is introduced into a further decomposition zone wherein remaining ammonium carbamate is substantially removed, and a third gas mixture thereby formed is processed to form a dilute aqueous ammonium carbamate solution. The remaining urea containing liquid phase is concentrated by evaporation in an evaporation zone. The evaporation zone includes a shell and tube heat exchanger wherein the urea containing liquid phase to be concentrated is introduced into the tube side of a first end of said exchanger, the second gas mixture is introduced into the shell side near the second end of said heat exchanger, and the dilute aqueous ammonium carbamate solution is fed into the shell side of said heat exchanger at a point between the first and second ends. Condensate formed in the shell side of the heat exchanger is discharged therefrom at the first end. In this manner, the heat of condensation of the condensing second gas mixture is transferred to the urea containing phase to be concentrated in the evaporation zone.

3 Claims, 2 Drawing Sheets

PROCESS FOR PREPARING UREA

This is a continuation of application Ser. No. 670,931, filed Nov. 13, 1984, abandoned.

BACKGROUND OF THE INVENTION

This invention relates to a process for preparing urea from ammonia and carbon dioxide.

If ammonia and carbon dioxide are fed into a synthesis zone under a suitable pressure (for instance 125-350 atm) and at a suitable temperature (for instance 170°-250° C.), first ammonium carbamate is formed in accordance with the reaction:

$$2\,NH_3 + CO_2 \rightarrow H_2N\text{---}CO\text{---}ONH_4$$

The resulting ammonium carbamate is subsequently converted to urea by dehydration according to the reaction:

$$H_2N\text{---}CO\text{---}ONH_4 \rightleftharpoons H_2N\text{---}CO\text{---}NH_2 + H_2O$$

The degree to which this conversion into urea proceeds depends, among other things, upon the temperature and amount of excess ammonia that is present in the synthesis zone. The resulting reaction product formed by this process is an aqueous solution substantially consisting of urea, water, ammonium carbonate, and uncoverted ammonia. This ammonium carbamate and the unconverted ammonia must be removed from the urea product solution, and they are most often recycled to the synthesis zone.

The synthesis zone may consist of separate zones wherein ammonium carbamate is primarily formed in the first zone and this ammonium carbamate is converted into urea primarily in the second zone. These zones, however, may also be combined in a single piece of apparatus.

One process for the preparation of urea which has found wide use in practical application is described in European Chemical News, Urea Supplement of Jan. 17, 1969, at pages 17-20. In the process there disclosed, the urea synthesis solution is formed in a synthesis zone maintained at a high pressure and temperature, and is thereafter subjected to a stripping treatment at synthesis pressure by heating the solution and contacting it countercurrently with a gaseous carbon dioxide stripping gas, so as to decompose a major part of the carbamate present therein. The gas mixture thus formed, containing ammonia and carbon dioxide, together with a small amount of water vapor and the carbon dioxide used in the stripping treatment, is removed from the remaining product stream and introduced into a condensation zone wherein it is condensed to form an aqueous ammonium carbamate solution. This aqueous carbamate solution, as well as the remaining non-condensed gas mixture, is recycled to the reaction zone for conversion to urea. The condensation of this gas mixture returned to the reaction zone provides the heat required for the conversion of ammonium carbamate into urea, and no heat need be supplied to the reaction zone from the outside. In addition to using carbon dioxide as the stripping gas as described in this publication, the stripping can also be carried out with gaseous ammonia, an inert gas or with a mixture of at least two of these gases.

The heat required for the stripping treatment is provided by the condensation of high pressure stream of 15 to 25 bar on the shell side of the tubes of the vertical heat exchanger in which the stripping is effected. The gas mixture obtained from this stripping treatment is mostly condensed in a first condensation zone wherein it is absorbed in an aqueous solution obtained from the further treatment of the urea-containing solution downstream. The aqueous ammonium carbamate solution thus formed, together with the remaining non-condensed gas mixture, are introduced into the synthesis zone for the formation of urea. In this synthesis zone, the heat required for the conversion of ammonium carbonate into urea is obtained by further condensation of this gas mixture to ammonium carbamate.

The stripped urea synthesis solution is subsequently expanded to a low pressure of, for instance, 2 to 6 bar, and introduced into a decomposition zone where it is heated by means of steam in order to remove a further amount of ammonia and carbon dioxide still remaining in the stripped urea solution in the form of ammonium carbamate. The resulting gas mixture, which also contains water vapor, is introduced into a second condensation zone wherein it is condensed and absorbed at a low pressure in an aqueous solution, and the dilute carbamate solution thus formed is pumped back to the high pressure section of the urea synthesis and eventually introduced into the synthesis zone. The remaining urea-containing product stream leaving this decomposition zone is subjected to further expansion and is concentrated to form a urea solution or melt that may be further processed to form solid product urea. To this end, the aqueous urea solution is evaporated, usually in two evaporation stages, and the resulting urea melt is processed to form granules, or the urea solution is crystallized. The gases obtained in the evaporation or crystallization, which contain in addition to water vapor an amount of ammonia, carbon dioxide, and entrained fine droplets of urea, are condensed to form process condensate. A part of this process condensate is used as absorbent for the gas mixture condensed in the second condensation zone. The remaining part can be treated with high pressure steam to hydrolyze the urea contained therein and to remove and recover the ammonia and carbon dioxide decomposition products, along with the ammonia and carbon dioxide that was already present.

It is known to incorporate into such a process an additional decomposition step in which further amounts of ammonium carbamate still present in the stripped urea synthesis solution are decomposed at an intermediate pressure of 12 to 25 kg/cm². In U.S. Pat. No. 4,354,040, the heat released upon condensation of such a gas mixture obtained in this additional decomposition step is transferred to the evaporation zone by means of passing a urea crystal suspension through the condensation zone via cooling tubes. In this manner, the heat from the condensation of this gas mixture is transferred to the crystal suspension to provide heat for the evaporation of water in the evaporation zone. However, the pumping and circulation of a crystal suspension through cooling tubes has several undesirable effects, including that the presence of solid particles gives rise to disturbances in the process operation, and erosion of the cooling tubes may occur. Moreover, in the process there described the heat absorbed by the crystal suspension is only partially utilized in the crystallization process, inasmuch as a part of the heated crystal containing solution is carried off as product.

It has furthermore been proposed to use the heat released in the condensation of such an intermediate pressure gas mixture containing ammonia and carbon dioxide for the concentration of a urea solution (see U.S. Pat. No. 3,366,682). This further known process does not involve a stripping treatment, but expands and heats the urea synthesis solution in two pressure stages, and the gases released in the expansion are separated from the respective remaining urea-containing solutions. The solution obtained in the first pressure stage, after separating off the gas mixture released upon expansion, is heated and the further gas mixture thus formed is passed in heat exchange with the urea solution to be evaporated, whereupon this solution is concentrated. The gas mixture is cooled as a result of this heat exchange, but is only partially condensed.

It has now been found that for the evaporation of urea solutions, a more economic utilization can be made of the heat released in the condensation of ammonia and carbon dioxide containing gas mixtures obtained in the urea preparation process at sufficiently high pressure levels, if the dew point of the gas mixture to be condensed is raised such that the gas mixture condenses virtually completely during the heat exchange. In this manner, not only is the sensible heat available, but also the heat of dissolution and the heat of condensation can be utilized almost completely in heat exchange with the evaporation stage.

SUMMARY OF THE INVENTION

The object of the present invention is to provide a process for preparing urea in which a more economic use is made in the evaporation stage of heat developed during processing of the urea synthesis solution. This is achieved in accordace with the present invention by decomposing the ammonium carbamate still present in the urea synthesis solution after the initial decomposition and removal of ammonium carbamate and unconverted ammonia therefrom, in at least two stages carried out at decreasing pressure levels, and thereafter substantially completely condensing the gases separated off at the first of these pressure levels, and transferring the heat thus released to the urea solution to be evaporated. In order to achieve virtually complete condensation, the dew point of this gas mixture to be condensed is raised by adding water or an aqueous solution, and the gas-liquid mixture thus formed is subjected to heat exchange with the urea solution to be evaporated.

The invention thus relates to a process for preparing urea wherein, in a synthesis zone, a urea synthesis solution containing ammonium carbamate and free ammonia is formed at a pressure of between about 125 and 350 bar and at a corresponding elevated temperature, from carbon dioxide and excess ammonia, a portion of this ammonium carbamate is decomposed in a first decomposition zone by the supply of heat, and the gas phase thus obtained is condensed in a first condensation zone. A further portion of the ammonium carbamate still present in the remaining urea containing solution is decomposed in a second decomposition by the supply of heat at a pressure of between about 4 and 40 bar, and the second gas mixture thus formed is separated off. The ammonium carbamate still present in the remaining urea containing stream is decomposed and removed in a further step, and the third gas mixture thus formed, containing ammonia and carbon dioxide, is separated off, and processed to form a solution of ammonia and carbon dioxide in water.

This process of the present invention is characterized by the improvement that the urea solution to be concentrated is introduced into the tubes of a shell and tube heat exchanger, said second gas mixture from the second decomposition step is fed into the shell side of the heat exchanger at the end opposite the place where the urea solution to be concentrated is fed, and the solution of ammonia and carbon dioxide in water formed by processing said third gas mixture is fed to the said shell side at a place located between the inlet for the second gas mixture and the inlet for the urea solution to be concentrated. The condensate formed within this heat exchanger is discharged from the shell side at the end where the urea solution is fed into the tubes.

In this manner, the dew point of the second gas mixture to be condensed is increased without a portion of its heat of condesation first being used to heat the dilute carbamate solution formed by processing the third gas mixture, which is supplied to this heat exchanger at a lower temperature. Instead, all of the heat available from this second gas mixture can be used to heat the urea solution to be evaporated. To optimize this advantage, it is preferable to feed this dilute carbamate solution step into the shell side of the heat exchanger at a place where the temperature in the shell side substantially corresponds to the temperature at which, in a Q-t-diagram, the condensation line of this gas mixture in the absence of the dilute carbamate solution, and the condensation line of the gas mixture in the presence of the dilute carbamate solution intersect, wherein Q is the amount of heat transferred from the shell side to the tube side, and t is the temperature in the shell side.

With the combination of measures proposed here, it is possible to make very efficient use of the sensible heat as well as the heat of condensation and the heat of absorption of the gas mixture from the second decomposition step. At relatively low pressures in the second decomposition step, within the limits indicated, this results mainly in an increase in the amount of exchangeable heat. At relatively high pressures in the second decomposition step, within the limits indicated, mainly an increase of the temperature difference between the shell side and the tube side of the heat exchanger is achieved, so that, for a given amount of heat to be transferred, a smaller heat transfer area will be sufficient. At higher pressures in the second decomposition step, the amount of gas mixture to be condensed, and hence also the amount of heat released in condensation, is smaller, and additional steam-heating of the urea solution may be necessary. Therefore, in general the pressure in the second decomposition step will be kept below 25 bar, more in particular between about 15 and 22 bar. In that case, a third decomposition step operated under a pressure of between about 1 and 10 bar is desired. However, it is also possible to operate the second decomposition step under a pressure of between 4 and 10 bar. In this case, the urea solution obtained in this step can be sent directly to the concentration step, where decomposition of the remaining carbamate and concentration then take place simultaneously.

If the decomposition of carbamate not converted to urea takes place in three steps, it is advantageous to lead the gas mixture to be condensed into the heat exchanger with a dew point of between 110° and 160° C., so that here, too, the temperature difference between the condensing gas and the urea solution to be evaporated in the top of the heat exchanger is above the minimum value at which heat transfer takes place. As a rule, it will suffice that the temperature of the gas mixture is between 125° and 180° C.

The process according to this invention can be advantageously applied in processes for the preparation of urea in which the decomposition of the ammonium carbamate is effected by stripping followed by heating in one or more pressure steps, as well as in processes wherein this ammonium carbamate decomposition is effected by heating the urea synthesis solution in a plurailty of pressure steps only.

DETAILED DESCRIPTION OF THE INVENTION

Figure 1:
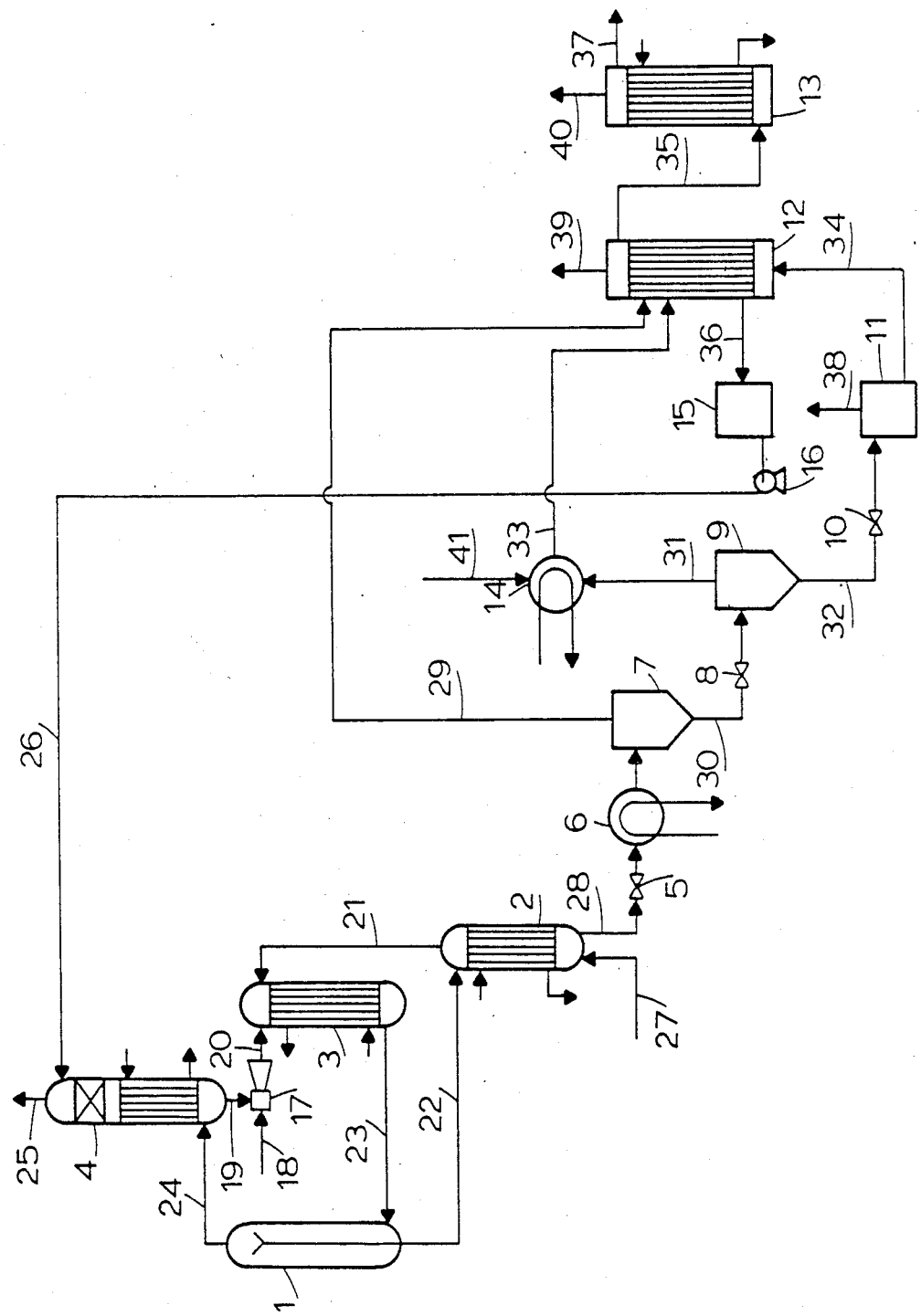
FIG. 1 schematically illustrates an embodiment wherein the improvement of the invention is incorporated in a process wherein the decomposition of the ammonium carbamate in the urea synthesis solution is first effected by stripping.

In the embodiment according to the figure, synthesis zone 1, first decomposition zone 2, shown as a stripping zone, first condensation zone 3, and scrubber 4 are all a part of the high pressure section of the urea synthesis process in which a pressure of, for instance, between about 125 and 350 bar is maintained. Expansion valves are indicated by 5, 8, and 10. Item 6 is a heating zone, 7 and 9 represent gas-liquid separators, and 11 is a storage tank for the urea solution to be evaporated. The first and second evaporation stages are indicated, respectively, by 12 and 13. Item 14 represents a second condensation zone, and 15 a storage tank for storage of the carbamate solution obtained in the heat exchange in the first evaporation stage. Item 16 is a pump for pumping ammonium carbamate solution, and 17 is a liquid ejector.

Ammonium carbamate solution from scrubber 4 is supplied through lines 19 and 20 into first condensation zone 3 through ejector 17 with the aid of liquid ammonia introduced through line 18. First condensation zone 3 is additionally fed through line 21 with the gas mixture from stripping zone 2. The gas mixture is obtained in stripping zone 2 by passing the urea synthesis solution, introduced through line 22, countercurrently to a gaseous carbon dioxide stripping gas introduced into this zone through line 27 while supplying heat, for instance by means of high pressure steam.

The first condensation zone may, for instance, be a vertical shell and tube heat exchanger. The heat released by this condensation and formation of ammonium carbamate is removed from the condensation zone by means of boiler feed water which is thereby converted into low-pressure steam of about 4 to 5 bar. The stripping zone 2 also can be designed as a vertical shell and tube heat exchanger. The heat required for the stripping can be supplied by means of high pressure steam of, for instance, 15–30 bar.

The ammonium carbamate solution formed in first condensation zone 3, together with remaining non-condensed gases, are supplied to synthesis zone 1 through line 23. In the synthesis zone, the heat developed by the further condensation of ammonia and carbon dioxide to ammonium carbamate is sufficient to provide the heat requirements for the endothermic conversion of ammonium carbamate into urea. The buildup of inert gases in the synthesis zone is prevented by purging a gas mixture containing ammonia, carbon dioxide, and inerts through line 24 and introducing it into scrubber 4 wherein the ammonia and carbon dioxide present therein are scrubbed out with the carbamate solution supplied through line 26. The inert gases are discharged through line 25. These inert gases are introduced into the process, for instance, with the fresh ammonia and carbon dioxide feeds, and possibly as passivating air or oxygen.

The stripped urea solution is removed from stripping zone 2 via line 28, is expanded in expansion valve 5 to a pressure of about 4 to 40 bar, for instance about 24 bar, and is heated in heating zone 6 to a temperature of between about 125° and 180° C., for instance about 165° C. As a result, a portion of the ammonium carbamate still present in this urea containing solution is decomposed, and the resulting gas-liquid mixture is introduced into gas-liquid separator 7. From this separator, a gas mixture containing substantially ammonia, carbon dioxide, and water vapor is carried off through line 29, and the residual liquid phase is removed through line 30, expanded through expansion valve 8 to a pressure of between about 1 and 10 bar, for instance about 7 bar, and the gas liquid mixture thus formed is introduced into gas-liquid separator 9. From gas-liquid separator 9, a gas mixture containing substantially ammonia, carbon dioxide, and water vapor is discharged through line 31 and introduced into second condensation zone 14 wherein it is condensed to form an ammonium carbamate solution with the aid of an aqueous solution, for example process condensate, supplied by line 41. The heat released as a result of this condensation is carried off by means of cooling water. The residual liquid phase obtained in gas-liquid separator 9 is discharged through line 32 and is further expanded in expansion valve 10 to atmospheric pressure or lower, for instance about 0.6 bar, and is thereupon directed to storage tank 11.

The solution in storage tank 11, containing for instance about 70 percent by weight urea, and still containing ammonia and carbon dioxide, is supplied through line 34 to first evaporation zone 12, wherein it is concentrated to, for instance, more than 90 percent by weight urea. This further concentrated urea solution is passed via line 35 to second evaporation zone 13. The heating means in these evaporation zones is, for the process of the invention, preferably designed as a vertical shell and tube heat exchanger. In principle, as a horizontal shell and tube heat exchanger can be used, but this requires a more complex construction of the apparatus. The water vapor obtained in these two evaporation zones, containing small amounts of liquid urea, ammonia, and carbon dioxide, removed through lines 39 and 40, respectively, together with the gas phase removed from storage tank 11 via line 38, are sent, after condensation, to an installation (not illustrated) for the processing of process condensate.

The heat required for the evaporation in the second evaporation zone 13 is supplied by means of condensation of low-pressure steam. The heat required in the first evaporation zone 12 is supplied by the condensation of the gas mixture discharged from gas-liquid separator 7 through line 29. Advantageously, this gas mixture is passed into the shell side of a shell end tube heat exchanger of the first evaporation stage 12, to which the ammonium carbamate solution from the second condensation zone 14 is simultaneously supplied through line 33. In this manner, the dew point of the gas mixture to be condensed therein is raised, and the carbamate solution functions both as a condensing agent as well as a solvent for the gas mixture to be condensed.

Preferably, the gas-liquid mixture is passed through the heating zone countercurrently to the urea solution to be evaporated. The ammonium carbamate solution formed in the shell side as a result of this condensation is passed through line 36 to storage tank 15 wherein it is brought up to synthesis pressure by pump 16 and passed through line 26 into the top of scrubber 4 wherein it is utilized for the scrubbing of ammonia and carbon dioxide from the inert-containing gas mixture removed from synthesis zone 1 via line 24.

The evaporated, concentrated urea solution is carried off through line 37 for use or further processing.

If the heat released by the condensation of the gas mixture supplied through line 29 is not sufficient to meet the total heat requirements of the first evaporation stage 1, any deficiency can be made up by the condensation of low-pressure steam. In that event, the shell side of the heating zone must be divided into two separated compartments.

Figure 2:
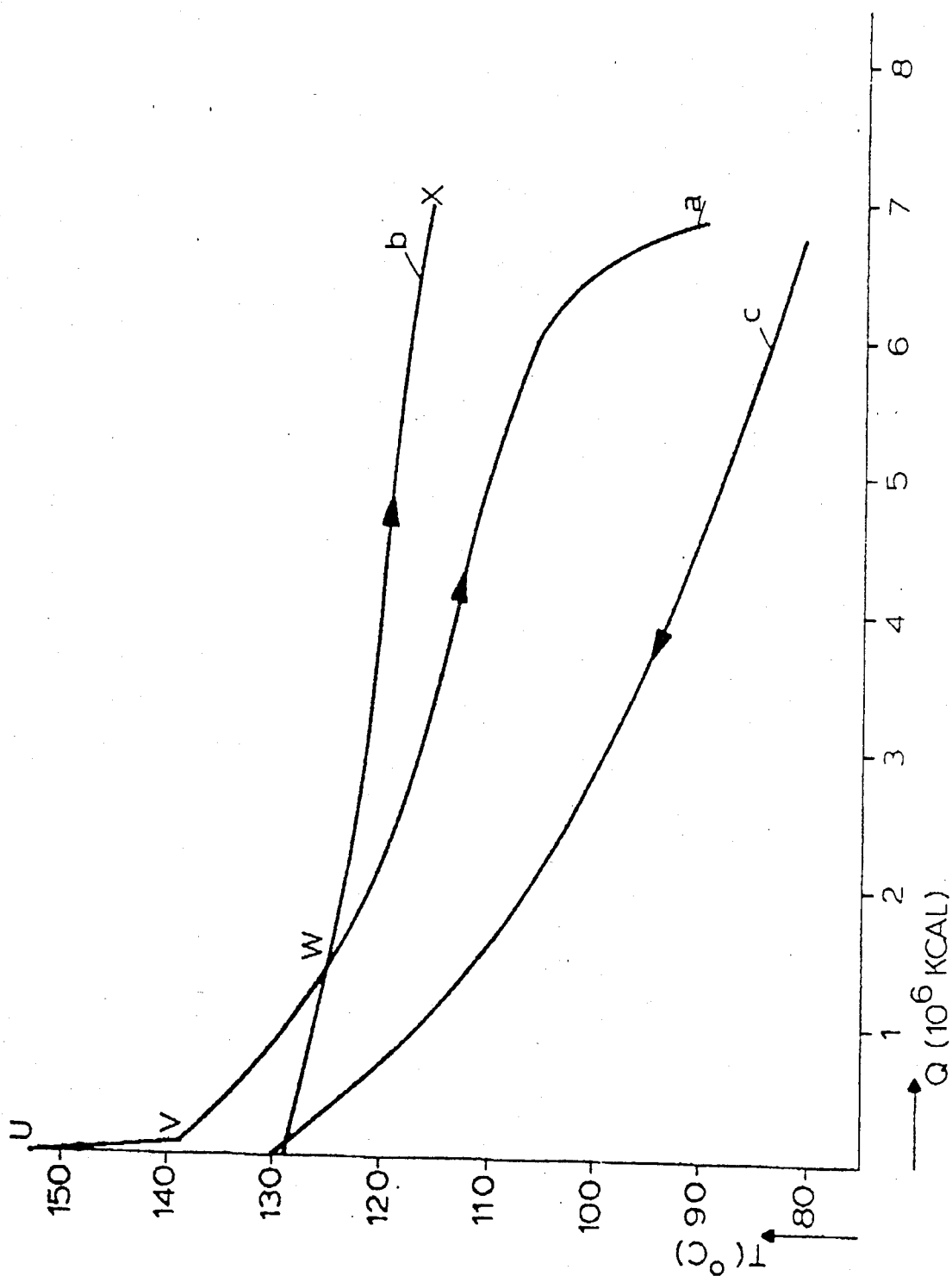
FIG. 2 represents a Q-t diagram.

FIG. 2 is a Q-t-diagram in which is represented, at a pressure of 18 bar, the condensation line of a gas mixture containing ammonia, carbon dioxide, and water vapor in the absence of a dilute aqueous carbamate solution (line a), as well as the condensation line of such a gas mixture in the presence of a dilute aqueous carbamate solution (line b). On the ordinate is plotted the heat released in the condensation and on the abscissa the condensation temperature. In this diagram also is represented the evaporation line of a urea solution to be evaporated (line c). When in the condensation of such a gas mixture an aqueous carbamate solution is added under circumstances represented in the diagram by the intersection point of the two condensation lines, this condensation goes along the line UVWX (U is the temperature at which the gas mixture is fed, V the dew point, W the intersection point of the condensation lines, and X is the temperature at which the condensate is discharged). From the diagram it can be seen that the temperature difference between the condensing gas mixture in the shell side of the shell and tube heat exchanger of the first evaporation stage and the urea solution to be evaporated in the tube section thereof is sufficient to realize a good heat exchange along the whole evaporation trajectory.

The invention will now be described in further detail by means of the following examples, but is not resticted thereto.

EXAMPLE I

Using the process of the invention, urea is prepared according to the embodiment represented in the figure in an installation having a production capacity of 1500 tons per day. All quantities are given in kg per hour. The pressure applied is 157.3 bar is the high-pressure section of the installation and 23.5 bar in the second decomposition step and in the shell side of the heater of the first evaporation stage.

The high-pressure section of the installation is supplied with 25,560 kg $NH_3$, which contains 107 kg $H_2O$ and which has been preheated to 85° C., and 38,681 kg of a carbamate solution containing 16,521 kg $CO_2$, 13,392 kg $NH_3$, and 8,228 kg $H_2O$. The temperature in the reaction zone is 183° C. and the molar ammonia to carbon dioxide ratio (N/C ratio) is 2.95. To the stripping zone 179,594 kg urea synthesis solution is supplied wherein it is stripped with 48,133 kg of a gas mixture containing 46,079 kg $CO_2$ and inert gases as the balance, mainly air. From the stripping zone 120,382 kg stripped urea synthesis solution containing 63,539 kg urea, 291 kg biuret, 15,556 kg $CO_2$, 13,193 kg $NH_3$, 27,775 kg $H_2O$, and 27 kg inert components are carried off.

The stripped urea synthesis solution is expanded to a pressure of 23.5 bar and heated to a temperature of 165° C. thereby decomposing a further amount of ammonium carbamate. The 24,183 kg of gas mixture thus obtained, containing 14,681 kg $CO_2$, 7,062 kg $NH_3$, 2,413 kg $H_2O$, and 27 kg inerts, is separated from the remaining liquid phase in a gas-liquid separator. The 96,199 kg of remaining liquid phase contains 63,539 kg urea, 291 kg biuret, 876 kg $CO_2$, 6,131 kg $NH_3$, and 25,362 kg $H_2O$. The pressure of this liquid phase is farther lowered to 6.9 bar, and the resulting gas-liquid mixture is passed into gas-liquid separator 9 wherein 4,392 kg of a gas mixture consisting of 552 kg $CO_2$, 2,612 kg $NH_3$, and 1,228 kg $H_2O$ is separated off. The pressure of the remaining solution is still further lowered to 0.65 bar, which yields 84,663 kg urea solution having a temperature of 90° C. and consisting of 63,477 kg urea, 324 kg biuret, 24 kg $CO_2$, 593 kg $NH_3$, and 20,245 kg $H_2O$.

The gas mixture obtained in gas-liquid separator 9 is condensed in the second condensation zone with the aid of a carbamate solution containing 2,059 kg $CO_2$, 2,875 kg $NH_3$, and 4,623 kg $H_2O$ formed in the working up of the process condensate. This condensation in the second condensation zone results in the formation of 15,750 kg of an ammonium carbamate solution having a temperature of 45° C. and consisting of 2,611 kg $CO_2$, 7,289 kg $NH_3$, and 5,850 kg $H_2O$. This solution is brought up to under a pressure of 23.5 bar and fed together with the gas mixture from gas-liquid separator 7, into the top of the shell side of the heating section of the first evaporating stage, countercurrently to the urea solution to be evaporated. The gas mixture is then condensed, in which process 38,861 kg carbamate solution with a temperature of 124° C. is formed. The urea solution passed through the tubes of the heating section is concentrated in this process and leaves the heater with a temperature of 130° C. The composition of this solution is 67,874 kg urea, 425 kg biuret, 216 kg $NH_3$, and 3,379 kg $H_2O$. From the top of the first evaporation step 17,798 kg vapor mixture escapes consisting of 16,774 kg $H_2O$, 275 kg $CO_2$, 581 kg $NH_3$, 23 kg inert, and 146 kg urea. If the heating of the first evaporation step is effected with low-pressure steam, 18,390 kg steam of 4 bar is required to obtain the same result.

EXAMPLE II

Urea is prepared according to the embodiment represented in the figure in an installation having a production capacity of 1000 tons a day. The quantities are given in kg per hour. In the second decomposition step, in which a pressure of 18 bar is maintained, a gas mixture is obtained containing 9,440 kg $CO_2$, 5,680 kg $NH_3$, and 1,810 kg $H_2O$. The temperature of this gas mixture is 153° C., its dew point is 139° C. This gas mixture is condensed with the aid of a carbamate solution having a temperature of 45° C. and containing 1,470 kg $CO_2$, 4,440 kg $NH_3$, and 4,470 kg $H_2O$ in the shell side of a vertical shell and tube heat exchanger which forms the heating section of the first evaporation step. To this end the gas mixture is fed into the top of the shell side, countercurrently to the urea containing solution to be evaporated which contains 41,667 kg urea, 132 kg $CO_2$, 1,343 kg $NH_3$, and 14,639 kg $H_2O$. This urea containing solution, which is passed through the tubes of the heating section, is concentrated by the heat released thereby to a 95 wt.-% urea solution, and leaves the heating section with a temperature of 130° C. If the heating of the first evaporation step is effected with low pressure steam, 13,100 kg steam of 4 bar is required to obtain the same result.

What is claimed is:

1. In a process for the preparation of urea from the reaction of carbon dioxide and a molar excess of ammonia in a synthesis zone at a pressure of between about 125 and 350 bar and at a corresponding elevated temperature, to form a urea synthesis solution containing unconverted ammonium carbamate and free ammonia, wherein in a first decomposition zone, urea synthesis solution is heated, thereby decomposing a portion of said ammonium carbamate, and a first gas mixture thus obtained is separated from a residual urea containing liquid phase and at least partially condensed in a first condensation zone;

in a second decomposition zone, maintained at a pressure of between about 4 and 40 bar, residual urea containing liquid phase from said first decomposition zone is heated, thereby decomposing a further portion of said ammonium carbamate, and a second gas mixture thus obtained is separated from a second residual urea containing liquid phase;

in a further decomposition zone, ammonium carbamate remaining in said second residual urea containing liquid phase is substantially removed from the urea-containing solution, and a third gas mixture thereby formed, containing ammonia and carbond dioxide, is processed to form a dilute aqueous ammonium carbamate solution; and in an evaporation zone, said urea containing solution is concentrated by evaporation of water to form a concentrated urea solution;

the improvement essentially comprising said evaporation zone including a shell and tube heat exchanger wherein:

said second gas mixture is introduced into the shell side of said heat exchanger, adjacent one end of said shell side, wherein it is condensed and the condensate thus formed is discharged from said shell side adjacent the opposing end thereof;

said urea containing solution to be concentrated is passed through the tube side of said heat exchanger countercurrent to the condensing gas mixture in said shell side; and said dilute aqueous ammonium carbamate solution is fed into the shell side of said heat exchanger at a point between the introduction of said second gas mixture and the discharge of said condensate, said point being selected such that the temperature at said point in said shell side subtantially corresponds to the temperature at which, in a Q-t-diagram, the condensation line of said second gas mixture in the absence of said dilute carbamate solution, and the condensation line of said second gas mixture in the presence of said dilute carbamate solution, intersect, on which diagram Q is the amount of heat transferred from the shell side to the tube side, and t is the temperature in said shell side;

whereby said second gas mixture is virtually completely condensed and the heat of condensation of said condensing second gas mixture is transferred to said urea containing liquid phase being concentrated in said evaporation zone.

2. The process of claim 1 wherein said second gas mixture to be condensed has a dew point of between about 110° and 160° C. at the time it is fed into the shell side of said heat exchanger.

3. The process of claim 1 wherein the pressure in said second decomposition zone and the shell side of said heat exchanger is selected such that said second gas mixture is obtained in a quantity which, when virtually completely condensed in the shell side of said heat exchanger, will transfer to said urea containing solution the amount of heat required to achieve the desired concentration of said concentrated urea solution by said evaporation of water.

* * * * *